United States Patent
Agarwal et al.

(10) Patent No.: US 6,730,332 B2
(45) Date of Patent: May 4, 2004

(54) HERBAL COMPOSITION HAVING ANTIALLERGIC PROPERTIES AND A PROCESS FOR THE PREPARATION THEREOF

(75) Inventors: Ravindra Kumar Agarwal, Bangalore (IN); Anurag Agarwal, Bangalore (IN)

(73) Assignee: Natural Remedies Pvt. Ltd., Bangalore (IN)

( * ) Notice: Subject to any disclaimer, the term of this patent is extended or adjusted under 35 U.S.C. 154(b) by 120 days.

(21) Appl. No.: 10/019,389

(22) PCT Filed: Feb. 23, 2001

(86) PCT No.: PCT/IN01/00021
§ 371 (c)(1),
(2), (4) Date: Dec. 28, 2001

(87) PCT Pub. No.: WO01/64163
PCT Pub. Date: Sep. 7, 2001

(65) Prior Publication Data
US 2003/0194452 A1 Oct. 16, 2003

(30) Foreign Application Priority Data
Feb. 28, 2000 (IN) .................................. 158/MAS/2000

(51) Int. Cl.[7] ............................................. A61K 35/78
(52) U.S. Cl. ..................... 424/769; 424/734; 424/756
(58) Field of Search ................................ 424/769, 734, 424/756

(56) References Cited

FOREIGN PATENT DOCUMENTS

WO          WO 01/64163 A2       9/2001

OTHER PUBLICATIONS

Akah, P. et al., "Evaluation of Nigerian Traditional Medicine: Effects of Gakani, a Herbal Anti–Asthmatic Drug," *Journal of Ethnopharmacology*, vol. 55, pp. 87–92 (1997).
Akhila, A. et al., *CROMAP*, vol. 6, No. 3, pp. pp. 143–156 (1984).
Atal, C. et al., *The Indian Journal of Pharmacy*, vol. 26, No. 3, pp. 80–81 (1964).
Atal, C. et al., "The Chemistry of Indian Piper Species," *Journal of Natural Products*, vol. 38, p. 256–264 (May–Jun. 1975).
Azeem, M. et al., "Effect of Terminalia Chebula Extracts on Frog Heart Muscle ($Na^+$, $K^+$, $Mg^{++}$) ATP–ase Activity," *Fitoterapia*, vol. LXIII, No. 4, pp. 300–303 (1992).
Barthakur, N. et al., "Nutritive Value of the Chebulic Myrobalan (Terminalia chebula Retz.) and its Potential as a Food Source," *Food Chemistry*, vol. 40, pp. 213–219 (1991).
Bhishagratna, K., "An English Translation of the Suśruta Samhita Based on Original Sanskrit Text With a Full and Comprehensive Introduction, Additional Text, Different Readings, Notes, Comparative Views, Index, Glossary and Plates," *Chowkhamba Sanskrit Studies*, vol. III, pp. 118–131 (1996).
Bhisagratna, "Bhāvaprakasa of ŚRĪ Bhāvamiśra," *The Kashi Sanskrit Series 130*, 11 pages (1980).
Bose, B. et al., "Pharmacological Study of Carica Papaya Seeds With Special Reference to its Anthelmintic Action," *Ind. J. Med. Sci.*, vol. 15, pp. 888–895 (1961).
Cannell, R. et al., "Results of a Large Scale Screen of Microalgae for the Production of Protease Inhibitors," *Planta Medica*, vol. 54, pp. 10–14 (1988).
Chakravarty, H., "Herbal Heritage of India," *Bull. Botan. Soc. Bengal*, vol. 29, pp. 97–103 (1975).
Chopra, R. et al., *Glossary of Indian Medicinal Plants*, pp. 10–11 (1956).
Cotran, R. et al., *Robbins Pathologic Basis of Disease*, 5th Edition, pp. 177–195, 355, 356, 382, 683, 689–693, and 741–742 (1994).
Dahanukar, S. et al., "Efficacy of Piper Longum in Childhood Asthma," *Indian Drugs*, vol. 21, pp. 384–386 (Jun. 1984).
Dahanukar, S. et al., "Evuluation of Antiallergic Activity of Piper Longum," *Indian Drugs*, vol. 21, pp. 377–380 (Jun. 1984).
Das, S.N. et al., "Effect of Pulmoflex (Research Name AAC–400) on Mast Cell Stabilization," *Indian J. Indg. Med.*, vol. 17, No. 1, pp. 79–82 (Apr. 1995–Sep. 1995).
Deka, L. et al., "Some Ayurvedic Important Plants From District Kamrup (ASSAM)," *Ancient Science of Life*, vol. 111, No. 2, pp. 108–115 (Oct. 1983).
Dhar, M. et al., "Screening of Indian Plants for Biological Activity: Part I," *Indian J. Exp. Biol.*, vol. 6, pp. 232–247 (Oct. 1968).
Farooqi, M. et al., *J. Sci. Industri. Res.*, vol. 21B, pp. 454–455 (Sep. 1962).
Fernandez, A. et al., "Asthma in Children, A Clinical Controlled Study of Piper Longum in Asthma," *Pediatric Clinics of India*, vol. 15, No. 4., pp. 45–52 (Oct. 1980).
George, M. et al., "Investigations on Plant Antibiotics," *J. Sci. Ind. Res.*, vol. 6B, No. 3, pp. 42–46 (Mar. 1947).

(List continued on next page.)

*Primary Examiner*—William R. A. Jarvis
(74) *Attorney, Agent, or Firm*—Merchant & Gould, P.C.

(57) ABSTRACT

The present invention relating to a herbal antiallergic composition which comprises a synergistic mixture of extracts from the fruits of *Terminalia chebula*, bark of *Albizia lebbeck*, *Terminalia bellerica* and *Emblica officinalis*. The present invention also contains the fruits of *Piper longum*, *Piper nigrum* and of rhizomes of *Zingiber officinale* and thoroughly mixed to get the final composition which has potent antiallergic activity. The invention also relates to a process for the preparation of such composition. The composition is particularly useful for the treatment of allergic conditions.

19 Claims, 1 Drawing Sheet

OTHER PUBLICATIONS

Figure 1:
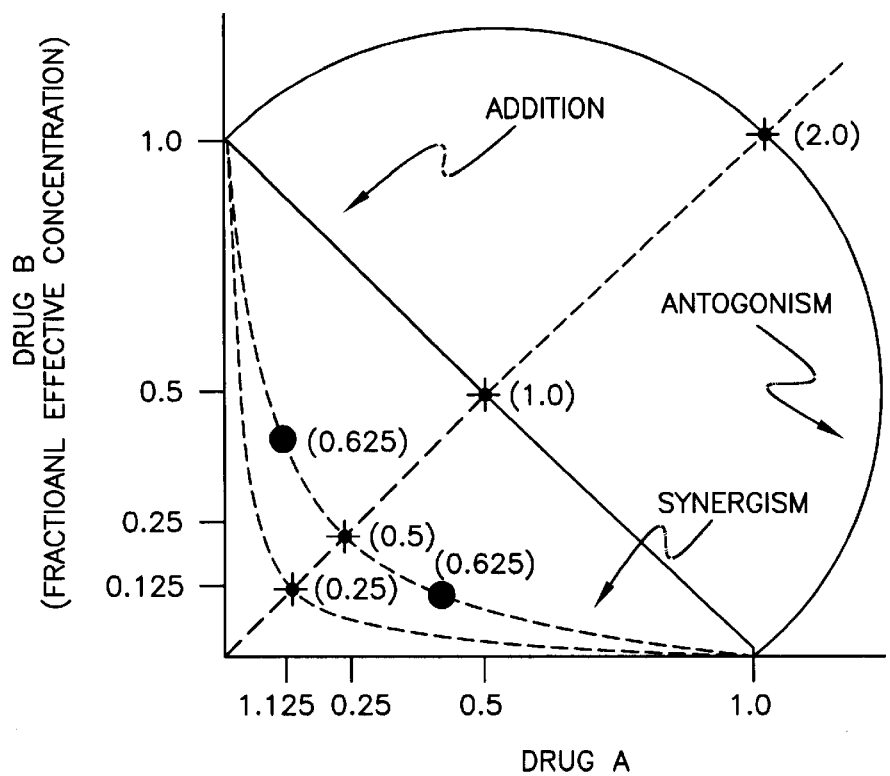

Ghooi, R. et al., "On the Antianaphylactic Activity of Swertia Chirata," *Allergy Apl. Immunol.*, vol. 15, pp. 53–59 (1981).

Ghosal, S., "Active Constituents of Emblica Officinalis: Part 1—The Chemistry and Antioxidative Effects of Two New Hydrolysable Tannins, Emblicanin A and B," *Indian Journal of Chemistry*, vol. 35B, pp. 941–948 (Sep. 1996).

Ghosh, M., *Fundamentals of Experimental Pharmacology*, 2nd Edition, pp. 34–39, 60–62, and 87–89, 1 (1984).

Ghosh, M., *Fundamentals of Experimental Pharmacology*, 2nd Edition, pp. 153–158 (1984).

Gokhale, A. et al., "Studies on Antiallergic Activity of Ethanolic Extract of Tephrosia Purpurea Linn," *Indian Drugs*, vol. 37, No. 5, pp. 228–232 (May 2000).

Goodman & Gilman's *The Pharmacological Basis of Therapeutics*, 8th Edition, pp. 1038–1039 (1986).

Goodman & Gilman's *The Pharmacological Basis of Therapeutics*, 9th Edition, 11 pages (1991).

Harrison's *Principles of Internal Medicine*, 14th Edition, vol. 1, pp. 20, 304–305, 309–310, 1421, 1754, 1774, 1843, 1860–1868 (1998).

*Harrison's Principles of Internal Medicine*, 14th Edition, vol. 1, pp. 1867–1869 (1998).

*Indian Medicinal Plants, a compendium of 500 species*, vol. 5, pp. 431–439 (1997).

*Indian Medicinal Plants, a compendium of 500 species*, Part 3 (Phyllanthus Emblica), pp. 256–263 (1997).

Iyengar, M. et al., "Studies on an Antiasthma Kada: A Proprietary Herbal Combination Part I Clinical Study," *Indian Drugs*, vol. 31, No. 5, pp. 183–186 (Mar. 1994).

Jamwal, K. et al., "Pharmacological Investigation of the Fruit of Emblica Officinalis Gaertn.," *J. Sci. Industr. Res.*, vol. 18C, pp. 180–181 (Sep. 1959).

*The Johns Hopkins Medical Handbook, The 100 Major Medical Disorders of People Over the Age of 50, Plus a Directory to the Leading Teaching Hospitals, Research Organizations, Treatment Centers, and Support Groups*, pp. 222–223, 226–227, 324–327 (1992).

Kato, K. et al., "Studies on Scavengers of Active Oxygen Species. 1. Synthesis and Biological Activity of 2–O–Alkylascorbic Acids," *Journal of Medicinal Chemistry*, vol. 31, No. 4, pp. 793–798 (1988).

Kholkute et al., "Short Communications," *Ind. J. Exp. Biol.*, vol. 17, pp. 289–290 (Mar. 1979).

Khorana, M. et al., "Expectorant Activity of Emblica Officinalis Gaertn.," *J. Sci. Industr. Res.*, vol. 19C, pp. 60–61 (Feb. 1960).

Kirtikar et al., *Indian Medicinal Plants*, vol. 2, pp. 1016–1019 (1981).

Kiuchi, F. et al., "Inhibitors of Prostaglandin Biosynthesis From Ginger," *Chem. Pharm. Bull.*, vol. 30, No. 2, pp. 754–757 (1982).

Kokate, C., *Pharmacognosy*, pp. 322–325 (1988).

Kulkarni, S., *Handbook of Experimental Pharmacology*, 2nd Edition, pp. 22–25 (1993).

Lee, Y. et al., "Antianaphylactic Activity of Poncirus Trifoliata Fruit Extract," *Journal of Ethnopharmacology*, vol. 54, pp. 77–84 (1996).

Martindale *The Extra Pharmacopoeia*, 30th Edition, pp. 1140–1146 (1993).

Meister, A. et al., "Antispasmodic Activity of Thymus Vulgaris Extract on the Isolated Guinea–Pig Trachea: Discrimination Between Drug and Ethanol Effects," *Planta Medica*, vol. 65, pp. 512–516 (1999).

Miśra, S. et al., *Bhāvaprakāśa of ŚRĪ Bhāva Miśra*, 5th Edition, 3 pages (1969).

Mujumdar, A. et al., "Effect of Piperine on Bioavailability of Oxyphenylbutazone in Rats," *Indian Drugs*, vol. 36, No. 2, pp. 123–126 (Feb. 1999).

Mukhopadhyay, B. et al., "Albizzia Lebbeck: A Remedy for Allergic Conjunctivitis," *Jour. Res. Edu. Ind. Med.*, pp. 17–23 (Oct.–Dec. 1992).

Nadkarni, K., *Indian Materia Medica With Ayurvedic, Unani–Tibbi, Siddha, Allopathic, Homeopathic, Naturopathic & Home Remedies, Appendices & Indexes*, vol. 1, pp. 480–485 (1993).

Nadkarni, K., *Indian Materia Medica With Ayurvedic, Unani–Tibbi, Siddha, Allopathic, Homeopathic, Naturopathic & Home Remedies, Appendices & Indexes*, vol. 1, pp. 1308–1315 (1993).

Nair, A. et al., "Studies on the Mast Cell Stabilizing Activity of Vitex Negundo Linn," *Indian Drugs*, vol. 32, No. 6, pp. 277–282 (1995).

Rajasekaran, M. et al., "Preliminary Communication: Mast Cell Protective Activity of Ursolic Acid—A Triterpene From the Leaves of Ocimum Sanctum L.," *J. Drug Dev.*, vol. 2, No. 3, pp. 179–182 (1989).

Ramachandra, L. et al., "Chemical Examination of Terminalia bellerica Roxb.," *Indian J. Chem.*, vol. 8, pp. 1047–1048 (Nov. 1970).

Rastogi, R. et al., *Compendium of Indian Medicinal Plants*, vol. 2, p. 671 (1991).

Reddy, M. et al., "A Survey of Plant Crude Drugs of Anantapur District, Andhra Pradesh, India," *Int. J. Crude Drug Res.*, vol. 27, No. 3, pp. 145–155 (1989).

Sastri, V., "Yogaratnākara with 'Vidyotini' Hindi Commentary," *The Kashi Sanskrit Series 160*, 7 pages (1960).

Satyavati, G. et al., *Medicinal Plants of India*, Indian Council of Medical Research New Delhi, vol. 2, pp. 427–428, 433–434, 448–455 (1987).

Satyavati, G. et al., *Medicinal Plants of India*, Indian Council of Medical Research New Delhi, vol. 2, pp. 428–430, 434–436, 448–455 (1987).

Shah, C. et al., "Pharmacognostic Study of Albizzia Lebbek Benth. Bark," *J. Sci. Industr. Res.*, vol. 19C, pp. 199–202 (Aug. 1960).

Sharma, P., *Caraka–Samhitā*, vol. 2, pp. 434–447 (1996).

Sharma, P., *Dravyaguna–Vijnana*, vol. 2, 4 pages (1993).

Shastry, V., *Bhavaprakasha Nighantu*, Motilal Banarasidas Publication, p. 9 (1988).

Sridharan, K. et al., "Chemical and Pharmacological Screening of Piper Nigrum L. Leaves," *Jour. Res. Ind. Med. Yoga & Homoeo.*, vol. 13, No. 4, pp. 107–108 (1978).

Sunanda et al., *Proceedings of 13th Annual Conference Indian Pharmacological Society*, p. 90 (1980).

Toyoda, I., "Antihistaminic Substance From Ginger," *Chem. Abst.*, No. 147, 33425m, 1 page (Apr. 1969).

*The Treatise on Indian Medicinal Plants*, vol. 2, pp. 61–62 (1992).

Tripathi, R. et al., "Further Studies on the Mechanism of the Anti–Anaphylactic Action of Albizzia Lebbeck, an Indian Indigenous Drug," *Journal of Ethnopharmacology*, vol. 1, pp. 397–406 (1979).

Tripathi, R. et al., "Studies on the Mechanism of Action of Albizzia Lebbeck, an Indian Indigenous Drug Used in the Treatment of Atopic Allergy," *Journal of Ethnopharmacology*, vol. 1, pp. 385–396 (1979).

Tripathi, S. et al., "Experimental & Clinical Studies on Adrenal Function in Bronchial Asthma: With Special Reference to the Treatment With Albizzia Lebbeck," *Quarterly Journal of Surgical Sciences*, pp. 169–176 (Mar. & Jun. 1978).

Tripathi, S. et al., "Studies on Anti–Asthmatic and Anti–Anaphylactic Activity of Albizzia Lebbeck," *Ind. J. Pharmac.*, vol. 9, No. 3, pp. 189–194 (1977).

Trivedi, V. et al., "A Clinical Study of the Anti–tussive and Anti–asthmatic Effects of Vibhitakphal Churna (Terminalia belerica Roxb.) in the cases of Kasa–Swasa," *Jour. Res. Ay. Sid.*, vol. III, No. 1 and 2, pp. 1–8 (1978).

Wealth of Asia, NISCOM, D–2.3, CSIR, (A. Lebbeck), New Delhi, 5 pages (1996).

Wealth of Asia, NISCOM, D–2.3, CSIR, (Chinese Ginger), New Delhi, 20 pages (1996).

Wealth of Asia, NISCOM, D–2.3, CSIR, (Emblica), New Delhi, 7 pages (1996).

Wealth of Asia, NISCOM, D–2.3, CSIR, (P. Nigrum), New Delhi, 6 pages (1996).

Wealth of Asia, NISCOM, D–2.3, CSIR, (P. Nigrum), New Delhi, 5 pages (1996).

Wealth of Asia, NISCOM, D–2.3, CSIR, (T. Bellirica), New Delhi, 7 pages (1996).

Wealth of Asia, NISCOM, D–2.3, CSIR, (T. Chebula), New Delhi, 16 pages (1996).

Winter, C. et al., "Carrageenin–Induced Edema in Hind Paw of the Rat as an Assay for Antiinflamatory Drugs," *Proc. Soc. Exp. Biol. Med.*, vol. 111, pp. 544–547 (1962).

HERBAL COMPOSITION HAVING ANTIALLERGIC PROPERTIES AND A PROCESS FOR THE PREPARATION THEREOF

This application is a 371 of PCT/IN01/00021, filed Feb. 23, 2001.

The present invention relates to an improved herbal composition having antiallergic properties, which is useful in the treatment of allergic conditions. The composition of the present invention is particularly useful for the treatment of allergic rhinitis, allergic bronchitis and bronchial asthma. This invention also relates to the process of preparing the antiallergic herbal composition.

INTRODUCTION TO ALLERGY

One of the common diseases that affects humankind is 'allergy' in its diverse manifestations. Allergy refers to any condition of the body mounting an attack on a specific foreign substance. People can experience allergic reactions to foods, chemicals, plants, animals and a variety of air borne substances. The substance to which the person is allergic is called the allergen. Allergy refers to a condition where in there is manifestation of conditions such as asthma, rhinitis, urticaria, and dermatitis alone or in combination. In majority of the cases there is a familial tendency. In most of the allergic individuals, there is an increase in levels of circulating IgE antibodies (special class of Immunoglobulins). Allergy is defined as a hypersensitivity or hyperimmunity caused by exposure to a particular antigen (allergen) resulting in marked increase in reactivity to that antigen/allergen upon subsequent exposure. This exposure sometimes results in harmful immunological consequences. Some common allergens responsible for allergy are dust, pollen, house-mites, grass weeds, pets, fungal spores, dust, etc. Sometimes corn, egg, soya, peanut, milk chocolate, caffeine, etc can be a source of food allergy.

An allergy is a state of altered immune response. The immune system's function is to identify and deal with the threats to the health. When a foreign body like dust or pollen enters the body, the exposure causes a reaction by the body. Usually the reaction itself is designed to rid the body of the allergens. This reaction can take many forms, one kind is an inflammatory reaction, the rushing of blood and/or mucus to the area of contact or site of invasion. This is healthy and normal. The increased blood supply to the affected area delivers healing nutrients, swelling, and heat may expel the invader and mucus may flush it out. Thus it acts as a protective phenomenon. But in the case of allergic individuals, this reaction persists for a longer time and causes inconvenience due to various clinical manifestations. An exaggerated defensive response by itself is the cause for this illness. A number of diseases like hay fever, bronchial asthma, urticaria and the like occur due to increased liberation of histamine or histamine like substances.

Air Borne/Inhalant Allergies

Headache, sneezing, watering of eyes, stuffy nose, wheezing and fatigue; these symptoms are the constant companions for an air borne allergy sufferer for several months (or more) every year. For those with perennial allergies, each day brings a cycle of misery, often broken only temporarily by powerful drugs like anti histaminics, steroids to suppress the immune system and decongestants, often with side effects like drowsiness etc. Air borne allergies usually affects the respiratory system. It involves sneezing, itching of throat and eyes, sinus headaches and sometimes coughing. Tree pollens, grass, weed pollens, pets, moulds, fungus, dust and cigarette smoke are common household allergens that can cause the allergic symptoms.

Pathogenesis of Allergy

On exposure to an antigen (allergen), special type of cells called antigen presenting cells carry the antigen, process it and present it to special type of white blood cells called T-lymphocytes [$TH_2$ subset of $CD_4$+T helper lymphocytes]. These T-lymphocytes respond by releasing important chemical mediators called cytokines like interleukins IL4, IL5, IL6 and granulocyte-macrophage colony stimulating factor (GM-CSF). The cytokines interact with B-lymphocytes (white blood cells) present in lymph nodes. The B-lymphocytes transform themselves into plasma cells, which secrete IgE antibodies. These are specific to the antigen. Once formed, the IgE antibodies have a strong tendency to get attached to a special group of cells called mast cells and basophils. Mast cells are located on the skin, Lung mucosa, bronchial mucosa, intestinal mucosa, lymphnodes, breast parenchyma and liver. They play a vital role in allergic and inflammatory phenomenon. A mast cell is a storehouse of 15–20 chemical mediators, which is responsible for clinical manifestations of allergy. On reexposure to allergen (antigen), the preformed IgE antibody on mast cell reacts with the antigen. The combination evokes a series of changes at the molecular level, which ultimately release the following mediators:

1) Histamine
2) 5-Hydroxytryptamine (Serotonin)
3) Leucotrienes $B_4$, $C_4$, $D_4$, $E_4$
4) Platelet activating factor
5) Prostaglandin $D_2$
6) Interleukins—IL-3, IL-4, IL-5, IL-6, Granulocyte macrophage colony stimulating factor (GMCSF), IL-1
7) Tumour necrosis factor-$\alpha$(TNF-$\alpha$)
8) Bradykinin etc.

Of all these mediators Leucotrienes $C_4$ & $D_4$ are the most potent vasoactive (capable of acting on blood vessels) and spasmogenic agents known. They increase the vascular permeability and cause vasodilatation and bronchial smooth muscle contraction. $LTB_4$ causes chemotaxis of neutrophils and eosinophils (white blood cells) which cause release of prostaglandin and bring about inflammatory changes. Prostaglandin $PGD_2$ causes broncospasm and increases mucus secretion. PAF (Platelet activating factor) causes platelet aggregation, release of histamine, broncospasm, increased vascular permeability and vasodilatation. It also acts as chemotactic for neutrophils and eosinophils. Therefore, it is important in late phase of inflammation. Cytokines like TNF, IL1, IL3, IL4, IL5, IL6 and GM-CSF are important cytokines that recruit inflammatory cells, which further cause degranulation. TNF-$\alpha$ is extremely important for attracting the cells at the site of inflammation.

Phenomenon of Allergy

Allergy is characterised by two distinct phases, the immediate phase and the delayed phase. The immediate phase includes the initial response that lasts for first 1–2 hours characterised by i) Vasodilatation, i.e. engorgement of the blood vessels that line the mucous membrane of the nose and
ii) Vascular leakage i.e. escape of plasma with proteins from the blood vessels. The mediators responsible are histamine and leucotrienes.

The delayed phase is the cellular phase or the inflammatory phase mediated by PAF, TNF, leucotrienes. On reexposure to allergen the preformed IgE antibody on mast cell reacts with the antigen. Unlike the protective inflammatory response in case of infections or any other trauma the phenomenon in case of allergy is different in that it is not self-limited. Antigen antibody reactions occur as long as the person gets exposed to allergen and as long as these reactions occur, the inflammation has to set in. As a result, the various effects of the cellular phase i.e. release of enzymes, free radicals, prostaglandins etc will continue to persist and cause persistent tissue damage, which eventually leads to chronic inflammation. Hence, a check is necessary. The main difference between allergy prone and non-allergy prone individuals is allergy prone individuals have been found to have an elevated IgE levels which means they over respond to antigenic stimulation unlike the other individuals. Further, i) The tendency for susceptibility is inherited.
ii) There is a deficiency of intracellular control of mediator release or synthesis or both or possibly, extra cellular control signals that generally bring mediator inactivation are impaired.

For more details, reference may be made to Robbins: Pathologic Basis for Disease, $5^{th}$ Edition 1994 W.B Saunder Company., Harrisons', "Principles of Internal Medicine". $14^{th}$ Edition, McGraw Hill Publications, 1998.

Allergic Rhinitis

Allergic rhinitis is a chronic inflammation of the mucus membrane lining the nasal passages that is caused by an allergic reaction. It is characterised by a stuffy, runny nose, frequent sneezing and a tendency to breathe through the mouth. Eyes may be red and watery. Headache, itchiness, nosebleeds and fatigue may be secondary complications. Some of the reasons for this condition could be exposure to wool, molds, feathers, dust and pollen etc.

Features of allergic rhinitis are:
1. Could be seasonal or chronic
2. Family history is often present
3. Increased levels of circulating IgE antibodies in such patients The present day therapy of allergic rhinitis includes:
Prevention of contact with allergen
Supportive therapy with anti-histaminics, decongestants, mast cells stabilizers and anti-inflammatory agents like corticosteroids.
Definitive therapy includes identification of the cause by intra-dermal injections of allergen and subsequent desensitization of the individual once the cause/allergen has been identified.

Despite having all the above therapies the cure for allergic rhinitis by the above related treatment is far from satisfactory. The process of desensitization is also expensive and complicated, requiring support of the patient with limited success. Hence, there is a need for alternative therapy.

Allergic Bronchitis/Bronchial Asthma

Bronchial asthma is actually improperly called reactive airway disease. It is usually an allergic response, some times to the same allergens that cause hay fever, and is often exacerbated by stress, exercise, infection, fumes, and cold air. It is characterized by symptoms like coughing, wheezing and breathlessness. These symptoms of an attack are caused by the contraction of smooth muscle of bronchial airways and by secretion of mucus that blocks the airway. Asthma is a disease of respiratory tract that causes breathing problems. These problems usually happen in episodes, also called attacks. Asthma is usually a chronic problem i.e., people who have asthma live with it everyday often for their whole life. It is serious, and it can be life threatening if not properly managed. However, with proper management most people with asthma can live normal, productive lives. Several factors have been suggested, such as an exposure to infections, and other triggers of allergens, and the quality of the air we breathe out doors and indoors. An asthma attack typically occurs when an allergen or irritant affects the sensitized lungs. Everyday life is filled with the allergens and other precipitating factors that can kick off an attack.

For example

Allergens: Pollens, feathers, moulds, animals, some foods, house dust.
Infections: Common cold, influenza.
Emotional stress and excitement.
Vigorous exercise.
Cold air.
Occupational dusts and vapors: Plastics, grains, metals, wood.
Air pollution: Cigarette smoke, ozone, sulphur dioxide, auto exhaust.
Sleep (nocturnal asthma).
Household products: paint, cleaners, sprays.
Drugs: aspirin, heart medications etc.

For more details, reference may be made to "The Johns Hopkins Medical Handbook" (1992) Published by Rebus, INC. New York.

Presently Available Therapies and Their Demerits

Intense research during the last several decades has highlighted the role of lymphocytes, immunoglobulin, mast cells and various autocoids in the pathogenesis of allergic conditions. Treatment of acute manifestations is limited to the use of adrenergic agents and adrenocorticoids for symptomatic relief. Antihistamines have limited utility. Isolated cases benefit from desensitization procedures, if the allergy is against a simple allergen. Various products have been used for the treatment of allergic conditions.

Presently some of the following therapies are used for the treatment of asthma/allergic bronchitis:
1. Bronchodilators like salbutamol, theophylline, which cause bronchial relaxation and reduce wheeze.
2. Anti histaminics like cetrizine, chlorpheniramine maleate etc., which block the effects of histamine on bronchial smooth muscle.
3. Corticosteroids which cause a reduction in immune mechanisms and act as anti-inflammatory agents.
4. Mast cell stabilizers like disodiumchromoglycate and ketotifen, which prevent the release of mediators from mast cells.
5. Supportive antibiotics as and when required, since infection can trigger or follow allergic bronchitis.

However, there are reports that prolonged using of these products can be harmful.

Each of these are having following restrictions.
Contraindications
Special precautions
Interactions highlighting potential hazards
Food interactions The adverse effects encountered with the above mentioned therapies are the following:
1. Bronchodilators—Salbutamol causes muscle weakness, tremors, hypokalemia, tachycardia etc. Theophylline has a narrow therapeutic index and can cause tachycardia, precardial pain etc.,
2. Antihistamanics—Cause sedation, tachycardia etc.
3. Corticosteroids:—Prolonged inhalation can cause oral thrush. Systemic absorption on long time oral medication can cause gastritis, osteoporosis, edema etc.,
4. Disodiumchromoglycate can cause cough wheezing, laryngeal edema headache rash etc.

For more details reference may be made to:
1. Harrisons', "Principles of Internal Medicine". $14^{th}$ Edition, McGraw Hill Publications, 1998.
2. Martindales The Extra Pharmacopoeia, $30^{th}$ Edition 1993.
3. Goodman Gillman's "The Pharmacological basis of Therapeutics" Mc Graw Hill, Newyork. Edition: Alfred Goodman Gillman, Theodore W. Rall, Alan S. Nies Palmer Jaylor. McGraw Hill Publications, 1991.

There are known herbal preparations described in ancient books which are useful in general, but are not meant specifically for allergy and asthma. In other words, these known preparations are used for variety of diseases. Further such preparations are used in crude forms, require high dosage, non palatable taste, and inconvenient dosage forms. In the case of certain other herbal preparations the efficacy of such preparations are not very well established.

In the present day, herbal products have become very popular because of their effectiveness along with minimum risk of side effects as compared to the synthetic products. Consequently research work based on various herbs for developing products for treating various diseases is in progress all over the world.

Need for Developing an Improved Herbal Composition for the Treatment of Allergic Conditions As explained above the synthetic products presently used for the treatment of allergic conditions have a good amount of side effects. An antiallergic product will be potent if it can modulate the immune system and reduce the sensitivity of the individual in such a way that less IgE secretion occurs and even if it occurs, the mast cells are stabilized.

The herbal kingdom offers few remedies for allergy. In natural therapy, certain herbal preparations were given mainly to boost the immune system of the body thinking that the altered immunity is the reason for allergy. However, the satisfaction of the patient was very low and these products use to seldom give appreciable relief. Owing to these reasons they never became popular with the patients.

The main objective of the present invention is therefore to provide an improved composition having profound antiallergic activity.

Another objective of the present invention is to provide an improved composition having anti allergic properties, which not only provides relief particularly in allergic rhinitis, allergic asthma and allergic bronchitis but also helps in correcting the underlying immunological disorders.

Still another objective of the present invention is to provide an improved herbal based composition having anti allergic properties which controls allergic manifestations like sneezing, stuffy nose, watering of eyes, itching in throat, eyes and nose, wheezing, breathlessness etc.

Another objective of the present invention is to provide an improved herbal composition having antiallergic properties, which does not cause drowsiness or immune separation unlike other chemical anti allergic compounds.

Another objective of the present invention is to provide an improved herbal composition having anti allergic properties which acts by mast cell stabilization i.e. by preventing the release of histamine which is responsible for manifestation of allergy. Still further objective of the present invention is to provide a process for the preparation of an improved herbal composition having anti allergic properties Development of the Invention The present invention is based on our experience and knowledge about the usage of various herbs along with our in depth studies on traditional literature. For this project a number of plants and plant preparations were selected for detailed studies. The selected plants/extracts were then subjected to the mast cell stabilization bioassay. This bioassay has been reported to be one of the important tools in detecting the substances having antiallergic activity. In this context reference may be made to "Rajashekharan M. et al, *J. Drug Dev.*, 1989, 2(3), 179–182." Mast cells are basophilic cells in subcutaneous and connective tissue. They are found in large numbers in mesentery of rats and contain numerous membrane bounded granules, which contain strong pharmacologically active mediators such as histamine, SRS-A, Serotonin, bradykinin etc. The role of mast cells in pathogenesis of allergic disease has been well recognized. Mast cells contain receptors for Fc fragment of IgE antibodies. Therefore, IgE antibodies formed on exposure to antigen will combine with the mast cells. On subsequent re-exposure to the same antigen, there occurs an antigen antibody reaction which will initiate mast cell de-granulation in a similar manner as that of de-granulating agents like carbachol or the compound which is the condensation product of N-methyl-p-methoxyphenylamine with formaldehyde. In this context reference may be made to Das S. N. et al. Ind. J. Indigenous. Medicine, April–September 1995; 17(1): 79–82.

Screening of Plants

Amongst the several plant extracts/plant fractions tested, we found that the following plants gave interesting results in the mast cell stabilization assay:

TABLE 1

| Test substances | $EC_{50}$ values (mcg/ml) |
|---|---|
| Water extract of *Terminalia chebula* fruits | 17.78 |
| Water extract of *Terminalia bellerica* fruits | 15.64 |
| Water extract of *Albizia lebbeck* bark | 17.78 |
| Water extract of *Emblica officinalis* fruits | 12.29 |
| Water extract of *Albizia chinensis* bark | 16.58 |
| Hydro alcoholic extract of *Terminalia chebula* fruits | 22.78 |
| Hydro alcoholic extract of *Terminalia bellerica* fruits | 24.56 |
| Hydro alcoholic extract of *Albizia lebbeck* bark | 56.49 |
| Hydro alcoholic extract of *Albizia chinensis* bark | 222.48 |
| Hydro alcoholic extract of *Emblica officinalis* fruits | 29.98 |
| Methanolic extract of *Terminalia bellerica* fruits | 95.48 |
| Methanolic extract of *Terminalia chebula* fruits | 58.98 |
| Methanolic extract of *Emblica officinalis* fruits | 42.46 |
| Methanolic extract of *Piper longum* | 33.93 |
| Methanolic extract of *Piper nigrum* | 13.96 |
| Methanolic extract of *Zingiber officinale* | 20.78 |
| Disodiumchromoglycate (standard) | 3.68 |

Our sustained research and studies based on the above results revealed that extracts of the plants having $EC_{50}$ values of more than 500 mcg/ml are not generally useful for antiallergic applications. Hence such plants were excluded from further research. From the above results it was also very clear that the extracts of *Terminalia chebula, Terminalia bellerica, Piper longum, Piper nigrum, Albizia lebbeck, Albizia chinensis, Zingiber officinale*, and *Emblica officinalis*, show promising mast cell stabilizing activity. Based on our above said findings we selected the above mentioned plants for the development of the present invention. Subsequent to the above said biological evaluation each of the extracts of the above said selected plants were analysed chemically. It also became clear from our studies that tannin bearing plants like *Terminalia chebula, Albizia lebbeck, Terminalia bellerica, Emblica officinalis, Albizia chinensis* show better activity when extracted with water while plants like *Piper longum, Piper nigrum* and *Zingiber officinale* show better activity when extracted with alcohol.

All the above mentioned plants which were short listed for developing the present invention have been well known in Ayurveda but their extracts in synergistic combinations having anti allergic activities, is hitherto not known and hence is novel. Given below are the information which are available in public domain on each of the selected plants used for the development of the present invention.

1) *Terminalia Chebula*

Part used: Fruits

Botanical description: Moderate or large deciduous tree, attaining a height of 25 to 30 mts. Leaves are 7 to 20 cms, glabrous, opposite, elliptic, oblong, rounded with acute apex. Flowers are bisexual and white or yellow in colour. Fruit is a drupe, pendulous, 2–4 cm long, obovoid from a broad base, glabrous. (Wealth of Asia, NISCOM, D-2.3, CSIR, New Delhi, 1996.)

Medicinal uses: Haritaki (*Terminalia chebula*) is an effective astringent and gargle for ulcerated surfaces, rejuvenative, tonic, laxative, nervine, expectorant and anthelmentic. It is indicated in cough, asthma, hoarseness of voice, hiccups. Fruits were used to treat cold along with pista, cloves and honey. Fruit powder is used in treating cough and asthma. (Wealth of Asia, NISCOM, CSIR, New Delhi, 1996; K. L. Bhishakratna, *Susrutha Samhita—Uttara tantra* p. 118–130; Mokhasmit, M. et al., *U.J. Med. Assocn.* Thailand, 1971, 54(7), 490–504; Reddy, M. B. et al., *Ind. J. Crud. Drug Res.* 1989, 27(3), 145–155; Azeem M. A. et al. *Fitoterapia*, 1992; 63(4): 300–303; Reddy, B. M., et al, *Int. J. Pharmacogn.*, 1994; 32(4), 352–35; *Yogaratnakara*, Chaukamba Pub., p. 320–330; *Bhavaprakasha* with Vaidyotini Commentary by Misra, B. S, "*Chikitsa Prakarana madhyama khanda*"—Chaukamba Pub, 1980; p. 683–701.

Phytochemistry: Fruits contain about 30% of astringent substances—chebulinic acid, tannic acid, gallic acid etc., resin and purgative principles of the nature of anthraquinones and sennosides are also present (Wealth of Asia, NISCOM, D-2.3, CSIR, New Delhi, 1996.).

Hydrolysable tannins like terchebulin, punicalagin and terflavin-A and phenolics like gallic acid, chebullic acid, di-ethyl ester of chebulic acid and ethyl ester of gallic acid have been reported to be isolated from fruits (Rastogi, R. P. et al, *Compendium of Indian Medicinal Plants*, 1991, Vol. 2, p. 671).

Pharmacology: It has been reported to exhibit antitussive and antihistaminic properties and has been used for bronchial asthma and chronic sinusitis. Its laxative property is used to treat constipation. Nutritive value of the chebulic myrobalan (*Terminalia chebula*) and its potential as a food source has been evaluated. The water and ethanolic extracts of the fruit on guinea pig ileum at a concentration of 0.01 gm/ml were found to have strong antihistaminic activity. (K. L. Bhishakratna, *Susrutha Samhita—Uttara tantra*, p. 118–130; Dhawan, B. N. et al. 'Screening of Indian Plants for Biological Activity', *Ind. J. Exp. Biol.*, 1968; 232–247; Mokhasmit, M. et al., *U. J. Med. Associ.*, Thailand, 1971; 4–57: 49–50; Tripathi, Y. N. et al., *Sachitra Ayur.*, 1983; 35(11): 733–740; Bharatkar, N. N. et al., *Food Chemistry*, 1991, 40(2), 213–219).

2) *Terminalia Bellerica*

Part used: Fruits

Botanical Description: A very large tree, with an erect trunk and large spreading head, flowering in the hot season, leaves crowded about the extremities of the branches, long petioled, oval to obvate or shortly acuminated, quite entire glabrous above and generally also beneath, 6 to 7 inches long by 2½ board, with 2 opposite glands on the upper side of the apex of the petiole and some times near the base, spikes axillary solitary simple erect almost the length of the leaves, flowers creamy white, the male towards the apex of the spike and shortly pedicellate, stamens 10, filaments 2–3 mm long, 8–12 cms long axillary spikes with a glandular disk at the bottom of the calyx, hermathrodite below and sessile ovary unilocular, two ovuled style 3–4 mm long, drupe obovate obscurely 5-angled, the size of a nutmeg, fleshly, brown pubescent. (Wealth of Asia, NISCOM, D-2.3, C.S.I.R., New Delhi, 1996.)

Medicinal use: It is employed in dropsy, piles, diarrhoea and leprosy; also occasionally in fever. When half-ripe it is used as a purgative due to the presence of oil that has properties similar to those of castor oil. On hydrolysis, the oil yields an irritant principle. (Wealth of Asia, NISCOM, D-2.3, C.S.I.R., New Delhi, 1996; Kirtikar & Basu, Vol-II, 1018–1019, *Yogaratnakara*, Chaukamba Pub., p. 320–330; *Bhavaprakasha* with Vaidyotini Commentary by Misra, B. S, "*Chikitsa Prakarana madhyama khanda*", Chaukamba Pub, 1980; p. 683–701.)

Phytochemisty: The fruits contain about 20 to 30% of tannins and 40 to 45% water-soluble compounds. The constituents include a green fixed oil, saponins, a resinous residue and three amorphous, hygroscopic glycosidal compounds and colouring matter. Tannins like phyllemblin, bellericannin, chebulagic acid and phenolics like gallic acid, ellagic acid, ethyl gallate have also been reported to be present in the fruits. The fixed oil contains esters of palmitic, stearic, oleic and linoleic acids. Triterpenes like belleric acid along with its glucoside bellericoside has been isolated from the fruits. (Kokate, C. K., *Pharmacognosy*, Nirali prakashan Pub., Pune, p. 323–324; Row and Murthy, "Chemical Examination of *Terminalia bellerica*", *Ind. J. Chem.*, 1970, 8, p.1047).

Pharmacology: Crude powder of the fruit is used for antitussive and antiasthmatic activity. The maximum tolerated dose of fruit extract was found to be 1000 mg/kg i.p. in mice. (Dhar et al. *Indian J. med. Res.*, 1969, 57, p.103; Trivedi, V. P et al., "Clinical study of the anti-tussive and anti-asthmatic effect of Vibhitakphal churna (*Terminalia bellerica*) in the cases of Kasa-swasa"*J. Res. Ayur. Siddha*, 1985, 3(142), p.1–8; Mokhasmit, M. et al. *U.J. Med. Ass.*, Thailand, 1971, 54(7), p.490–504.)

3) *Emblica Officinalis*

Synonym: *Phyllanthus emblica*

Part used: Dried fruit

Botanical description: A small to medium sized deciduous tree, 8–18 meters height with thin light grey bark exfoliating in small thin irregular flakes, leaves are simple, sub-sessile, closely set along the branchlets, light green having the appearance of pinnate leaves; flowers are greenish yellow, in axillary fascicles, unisexual, males numerous on short slender pedicels, females few, sub-sessile, ovary 3-celled; fruits globose, fleshy, pale yellow with six obscure vertical furrows enclosing six trigonous seeds in 2-seeded 3 crustaceous cocci. (The Wealth of Asia, NISCOM, D-2.3, C.S.I.R., New Delhi, 1996).

Medicinal uses: The fruits are sour, astringent, bitter, acrid, sweet, cooling, anodyne, ophthalmic, carminative, digestive, stomachic, laxative, alterant, aphrodisiac, rejuvenative, diuretic, antipyretic and tonic. They are useful in vitiated conditions of tridosha, diabetes, cough, asthma, bronchitis, cephalalgia, ophthalmopathy, dyspepsia, colic, flatulence, hyperacidity, peptic ulcer, erysipelas, skin diseases, leprosy, haematogenesis, inflammations, anemia, emaciation, hepatopathy, jaundice, strangury, diarrhoea, dysentery, hemorrhages, leucorrhoea, menorrhagia, cardiac disorders, intermittent fevers and greyness of hair. (The Wealth of Asia, NISCOM, D-2.3, C.S.I.R., New Delhi, 1996; *Indian Medicinal Plants—A compendium of 500 species*, Part 3, Orient Longman Publications, 1997, page 256–263; Shastry V. D., *Bhavaprakasha Nighantu*, Motilal Banarasidas Publication, 1988, page 9; Nadkarni K., *Indian Materia Medica*, Popular Prakashan, 1993 Vol. 1, p. 480.)

Pharmacology: The fruit extract has been tested for their expectorant activity and the activity was found to be due to direct stimulation of bronchial glands. The product is not reported to have any side effects even after prolonged use. (Nadkanmi K. M. *Indian Muteria Medica*, Vol. 1, Popular Prakashan, 1993, p. 480; Khorana, M. L. et al., *J. Sci. Industr. Res.*, 1960; 19(C): 60–61; Deka, A. et al., *Ancient Science of Life*. 1983, 3(2),108–115).

Phytochemistry: The fruits of *Emblica officinalis* are rich in tannins. The fruits have 28% of the total tannins distributed in the whole plant. The fruits have been reported to contain two hydrolysable tannins Emblicanin A & B, which have antioxidant properties, one on hydrolysis gives gallic acid, ellagic acid and glucose wherein the latter gives ellagic acid and glucose. Phyllemblin, Punigluconin Pedunculagin, were also reported to be isolated from fruits. The tannins are having the molecular weight ranging from 750–850. Apart from L-ascorbic acid, Emblica fruits also contain 'ascorbigen', an indole containing derivative of L-ascorbic acid (Vitamin C). Ascorbigen and its derivative N-methylascorbigen represent a new class immunomodulators. (The Wealth of Asia, NISCOM, D-2.3, C.S.I.R., New Delhi, 1996; Jaiswal, K. S. et al., *J. Sci. Industr. Res.*, 1959; 18(9): 180–181; Bose B. C. et al., *Ind. J. Med. Sci*, 1961; 15: 888; Ghosal S. et al. "Active constituents of *Emblica officinalis*—Part 1, The chemistry and anti-acidity effects of two new hydrolysable tannins, Emblicannin—A & B," *Ind. J. Chem.*, 1996, Vol. 35B, pg. 941–948.

4) *Piper Longum*

Part Used: Fruits

Botanical Description: A slender aromatic climber, rooting at the nodes, the branches erect, subscandent, swollen at the nodes; leaves alternate, lower ones broadly ovate, cordate, upper ones oblong, oval, all entire, smooth, thin with reticulate venation, veins raised beneath; flowers in solitary spikes; fruits berries, small, red when ripe, completely sunk in solid fleshy spike. (The Wealth of Asia, NISCOM, D-2.3, C.S.I.R., New Delhi, 1996).

Medicinal use: The fruits as well as roots are attributed with numerous medicinal uses, and are used for diseases of respiratory tract, viz., cough bronchitis, asthma, etc. It is used as a counter-irritant and analgesic when applied locally for muscular pains and inflammation; as snuff in coma and drowsiness and internally as carminative; as sedative in insomnia and epilepsy and as general tonic and haematinic (The Wealth of Asia, NISCOM, D-2.3, C.S.I.R., New Delhi, 1996).

Pharmacology: Rhizomes of *Zingiber officinale* and leaves of *Adhatoda vasica* along with fruits of *Piper longum* is used to treat bronchial asthma. Dried Fruit mixed with honey are used to treat cough and generally used for cold as a home remedy. (The Wealth of Asia, NISCOM, D-2.3, C.S.I.R., New Delhi, 1996; Satyavati, G. V. et al. *Medicinal Plants of India*, ICMR, New Delhi: 1987; Vol-2, p. 426; Dhar et al., *Ind. J Exp. Biol.*, 1968, 6, 232; Reddy M. B. et al., 'A Survey of Plant crude drugs in Anantpur district, Andhra Pradesh. India', *Int J Crude Drug Res.*, 1989, 27(3), 145–155). In view of the therapeutic use of *Piper longum* in bronchial asthma by Ayurvedic physicians, studies have been carried out on the mechanism of its anti allergic effects, as milk extract effectively reduced passive cutaneous anaphylaxis in rats and protected guinea pigs against antigen induced bronchospasm. (Dahanukar, S. A., et al. '*Piper longum* in childhood asthma', *Indian Drugs*, 1984, 21, 384; Dahanukar, S. A et al. "Evaluation of Antiallergic activities of *Piper longum,*" *Indian Drugs*, 1984, 21, 377–380). *Piper longum* has been advocated for prophylactic treatment of asthma in Indian traditional medicine. It was shown highly effective in decreasing frequency and severity of attacks in childhood asthma. In addition, sensitivity test, serum IgE & pulmonary functions all showed significant improvement after treatment with *Piper longum*.

The fruits are attributed with numerous medicinal uses, and may be used for diseases of respiratory tract viz., bronchitis, asthma (The Wealth of Asia, NISCOM, D-2.3, C.S.I.R., New Delhi 1996). Evaluation of antiallergic activities of *Piper longum* is carried out by rat lung perfusion (Sunanda et al., Proceedings of 13$^{th}$ Annual Conference Indian Pharmacological Society, 1981). In case of bronchial asthma, significant effect in controlling the frequency and severity of the asthmatic attack was observed. (lesnanduz et al., *Pediatric Clinic*, India, 1980; 15(4): 45.

Phytochemistry: The fruits contain 1% volatile oil, resin, alkaloids piperine and piperlonguminine, a waxy alkaloid N-isobutyldeca-trans-2-trans-4-dienamide and a terpenoid substance. (Atal, C. K. et al., *Ind. J. Pharm.*, 1964; 26: 80).

5) *Piper Nigrum*

Part used: Fruits

*Piper nigrum* is used widely as a household spice. Several studies have reported enhancement of blood levels of drugs when co-administered with Piperine. It was recognized that altered drug effects arise as a consequence of a change in bioavailability. In Indian medicine it is much employed as an aromatic stimulant in cholera, weakness following fevers, vertigo etc as a stomachic in dyspepsia and flatulence, as an anti periodic in malarial fever and as an alternative in paraplegia they are useful in arthritis, asthma, fever, cough, catarrh, dysentery, flatulence, cough.

Botanical Description: A climbing perennial shrub. Branches are stout, trailing and rooting at the node. Leaves entire, variable in breadth, 12.5–17.5 cm by 5.0–12.5 cm. Flowers are minute in spikes, usually dioecious, often female bears 2 anthers and the male, a pistillode. Fruiting spikes are variable in length. Fruits are globose and bright red when ripe and it is described as drupe, seeds usually globose. (The Wealth of Asia, NISCOM, D-2.3. C.S.I.R., New Delhi 1996).

Medicinal use: In Indian medicine, it is much employed as an aromatic stimulant, in cholera, and in weakness following fevers, vertigo, coma, etc., as a stomachic in dyspepsia and flatulence, as an antiperiodic in malarial fever. It is also used as an alterative in paraplegia and arthritic diseases. Externally, it is valued for its rubefacient properties and as a local application for relaxed sore throat, piles and some skin diseases. (The Wealth of Asia, NISCOM, D-2.3, C.S.I.R., New Delhi 1996, *Yogaratnakara*, Chaukamba Publications., p. 320–330; *Bhavaprakasha* with Vaidyotini Commentary by Misra, B. S; *Chikitsa Prakarana madhyama khanda*—Chaukamba Publications, 1980, p. 683–701; Sharma P. V., *Charaka Samhita—Chikitsa Stana*, Chaukamba Publications, 1996; p. 434–447).

Pharmacology: It has anti-allergic activity. Piperine strongly inhibits hepatic arylhydrocarbon hydroxylase and UDP-glucuronyl transferase activities, thus prolonging hexabartital sleeping time and zoxazolamine paralysis time in mice. Piperine enhanced the bioavailability of oxyphenylbutazone and thereby potentiated its anti-inflammatory activity in rats. (Kholkute, et al., *Ind. J. Exp. Biol.*, 1979; 17 289–290; George et al., J. Sci. Ind. Res., 1947, 6B, 42; Satyavati, G. V., "*Medicinal Plants of India*", ICMR, New Delhi. 1987; 2: 426; Dhar et al. *Ind. J. Exp. Biol.*, 1968; 6, p.232; Majumdar, A. M. et al., "Effect of piperine on bioactivity of oxyphenylbutazone in rats", *Indian Drugs*, 1999; 36(2), 123–126)

Phytochemistry: Pepper contains volatile oil, the crystalline alkaloids, piperine, piperidine, piperettine and a resin. The minor alkaloids present are piperitine, piperolein A, piperolein B, piperanine, trichostachine. The volatile oil contains large amounts of terpenes, and a α-pinene, phellandrene, dipentene and sesquiterpenes. The pungency is ascribed to piperine and the resin. They do not have any of the alkaloids and isobutyl amides found in the fruit (Atal, C. K. et al., *Lloydia*, 1962; 38: 256; Jennings, W. G. et al. *Food Science*, 1962; 26: 499; Sridharan K. et. al.,*J. Res. Ind. Med. Yoga Homeo*, 1978; 13: 4).

6) *Zingiber Officinale*

Part used: Rhizome

Family: Zingiberaccae

Botanical description: A herbaceous rhizomatous perennial, reaching up to 90 cm in height under cultivation. Rhizomes are aromatic, thick lobed, pale yellowish, bearing simple alternate distichous narrow oblong lanceolate leaves. The herb develops several lateral shoots in clumps, which begin to dry when the plant matures. Leaves are long and 2–3 cm broad with sheathing bases, the blade gradually tapering to a point. Inflorescence solitary, lateral, radical, pedunculate oblong-cylindrical spikes. Flowers are rare, rather small, calyx superior, gamosepalous, three toothed, open splitting on one side, corolla of three subequal oblong to lanceolate connate greenish segments. ((The Wealth of Asia, NISCOM, D-2.3, C.S.I.R., New Delhi 1996).

Traditional use: Ginger is carminative, pungent, stimulant, used widely for indigestion. It is chiefly used to cure diseases due to morbidity of Kapha and Vata. Ginger with lime juice and rock salt increases appetite and stimulates the secretion of gastric juices. It is said to be used for chronic bronchitis, common cold, chest congestion, cough, difficulty in breathing, dropsy, sore throat, throat ache, stomach ache, vomiting and rheumatism. Ginger forms an important constituent of many pharmacopoeial Ayurvedic formulations. (Misra B, *Bhavaprakasha Nighantu*, 5$^{th}$ edition, 1969, p.14; Sharma P. V. *Dravyagunavignani*, Part II, Chaukamba Publications, 1993, p. 331; *Indian Medicinal Plants, A Compendium of 500 species*, Part V, by Orient Longman Publications, 1997, p. 431; Nadkarni, *Indian Materia Medica*, Vol. I, 1993, p.1308; *Yogaratnakara*, Chaukamba Publications, p.320–330; *Bhavaprakasha* with Vaidyotini Commentary by Misra, B. S; *Chikitsa Prakarana madhyama khanda*—Chaukamba Publications, 1980; p. 683–701.

Phytochemistry: Ginger has been reported to contain usually 1–3% of volatile oil, pungent principles viz., gingerols and shogaols and about 6–8 lipids and others. Ginger oil contains zingiberene and bisaboline as major constituents along with other sesqui and monoterpenes. Ginger oleoresin contains mainly the pungent principles gingerols and shogaols as well as zingiberone. Shogaols have recently been found twice as pungent as gingerols. (Kiuchi F, et al., *Chem. Pharm. Bull*, 982, 30, 754; Wagner H, et al, *Plant Drug Analysis*, Springer, 1996, 300; Akhila A & Tewari. CROMAP, 1984, 6(3), 143–156).

Pharmacology: It is used for common colds due to pathogenic wind cold, characterized by severe intolerance to cold, slight fever, headache, general ache, nasal congestion and a running nose. Antihistamine activity has been studied in ginger. *Zingiber officinale* was indicated in allergic conditions in traditional text. However, they were following crude methods. Toyoda J., 'Antihistamine substance from ginger', Chem. Abst., 1969, 71, 33425; *Yogaratnakara* Chaukamba Publications, p.320–330; *Bhavaprakasha* with Vaidyotini Commentary by Misra, B. S; *Chikitsa Prakarana madhyama khanda*—Chaukamba Publications, 1980; p. 683–701.

7) Albizia Species: For Example *Albizia chinesis, Albizia lebbeck*

Part Used: Bark

Botanical description: It is a large, erect, unarmed, deciduous, spreading tree common all over India. It is found in the plain up to 900 m in the Himalayans and in the Andamans. Also known as the East Indian walnut or Sirish (Hindi). The tree prefers moist situations and is found to grow on a number of soils. (The Wealth of Asia, is NISCOM, D-2.3, C.S.I.R., New Delhi, 1996).

Medicinal use: Albizia species are known plants in the literature of Indian medicine, for diseases like bronchial asthma, utricaria and insect bites. The protective action of the Albizia species on adrenals against histamine is established which can be favorably utilized for the treatment of bronchial asthma and other allergic disorders. (The Wealth of Asia, NISCOM, D-2.3,., C.S.I.R., New Delhi, 1996; Tripathi S. N. et al., *Quart. J. of Surgical Science*, 1978, March–June, p.170–176; Shah & Bhattacharyya, *J. Sci. Industr. Res*. 1960, 19C, p.199; Farooqi & Kaul, ibid, 1962, 21B, p.454; Chakravarty, *Bull. Bot. Soc.*, Bengal, 1975, 29, p.97).

The plant is reported to have antiseptic, anti-dysenteric and anti-tubercular properties. The bark has acrid taste. It is recommended for bronchitis, leprosy, paralysis and helminth infections. The bark and seeds are astringent, useful in piles and diarrhoea, and act as tonic and restorative.

The water extract has been used as a traditional remedy for bronchitis, leprosy, gum inflammations and helminth infections. (Chopra R. N., et al., *Glossary of Indian Medicinal Plants*, 1956, p.11)

Pharmacology: A decoction of the bark and flowers protects the guinea pig against histamine as well as acetylcholine induced bronchospasm. Prolonged treatment with bark decoction protects the sensitized guinea pigs against antigen challenge. (Tripathy & Das, *Indian J. Pharmacol.*, 1977; 9; p.189). The bark is used as one of the ingredients of an Ayurvedic Kada or decoction used for treating asthma. Pharmacologically it was found to show antitussive action and the ability to prevent allergy-induced bronchospasm. The bark is also useful in the treatment of allergic conjunctivitis. (Iyengar et al, *Indian Drugs*, 1994, 31, 183, 187; Mukhopadhyay et al, J. Res. Educ. Ind. Med., 1992, 11 (4), p.17). The use of Albizia species decoction in the treatment of allergy is of great interest on several reasons viz., easy availability from natural sources, simple methods of preparation and drug administration and multi pronged activity i.e. inhibition of the sensitization process, anti body synthesis and mast cell degranulation. Anti-anaphylactic activity: Shows the effectiveness of water extract in anti-anaphylactic activity in guinea pig and rats. (Tripathi R. M., et al., *Journal of Ethnopharmacol.* 1979; 1: p.397–406). The effectiveness of the species of Albizia extract in the induced condition in guinea pigs was studied and its effect was found to be good. Also 60 patients of Bronchial asthma when treated, drop in histamine levels after treatment, was also found to be good (Tripathi S. N., et al., *Quart. J. of Surgical Science*, 1978, March–June, p.170–176). Atopic Allergy: The effect of extract of species of Albizia on the degranulation rate of peritoneal mast cells of albino rats was studied (Tripathi R. M, et al., *Journal of Ethnopharmocol.*, 1979, 1, p.385–396) and the result was very encouraging.

Phytochemistry: The bark yielded tannins of condensed type, viz., D-Catechin, Lebbecacidin (8,3',4'-tetrahydroxyflavan 3,4-diol). Isomers of leucocyanidin (5,7,3',4'-tetrachydroxy flavan -3,4-diol), (-)-melacadidin (7,8, 3'4,'-tetrahydroxyflavan-3,4-diol) in addition to friederein and β-Sitosterol. (Chatterjee, A., et al., *The Treatise of Indian Medicinal Plants*, 1992, Vol2, p.61–62). In another study, the bark yielded tannins (7–11%) of condensed type, viz. D-catechin, isomers of leucocyanidin (5,7,3',4'-tetrahydroxyflavan-3,4-diol) and (-)-melacacidin (7,8,3',4'-tetrahydroxyflavan-3,4-diol) and a new leucoanthocyanidin, lebbecacidin (8,3',4'-trihydroxyflavan-3,4-diol). It also gives friedelin and β-sitosterol. Extract of the bark possesses anthelmintic activity and expectorant action. (The Wealth of Asia, NISCOM, D-2.3, CSIR, New Delhi, 1996).

Development of Synergistic Combinations of the Present Invention

The extracts of the above mentioned plants were then blended in several prototype combinations and each of these combinations were again subjected to the mast cell stabilization assay. The prototype combinations were prepared using the isobologram technique such that the resulting combinations have synergistic antiallergic activity. As per the isobologram technique, increasing concentrations of one ingredient were plotted against the increasing concentrations of another ingredient, as shown in FIG. 1. In this context reference may be made to "Goodman & Gillman's 'The Pharmacological Basis of Therapeutics', Vol. 2, 8$^{th}$ Edition, page 1038, edited by Alfred Goodman Gillman et al., 1992, published by McGRAW-HILL, INC. Singapore". Each of these combinations thus prepared were subjected to the mast cell stabilization assay and the synergistic combinations were selected for further compatibility studies with other ingredients.

Figure 2:
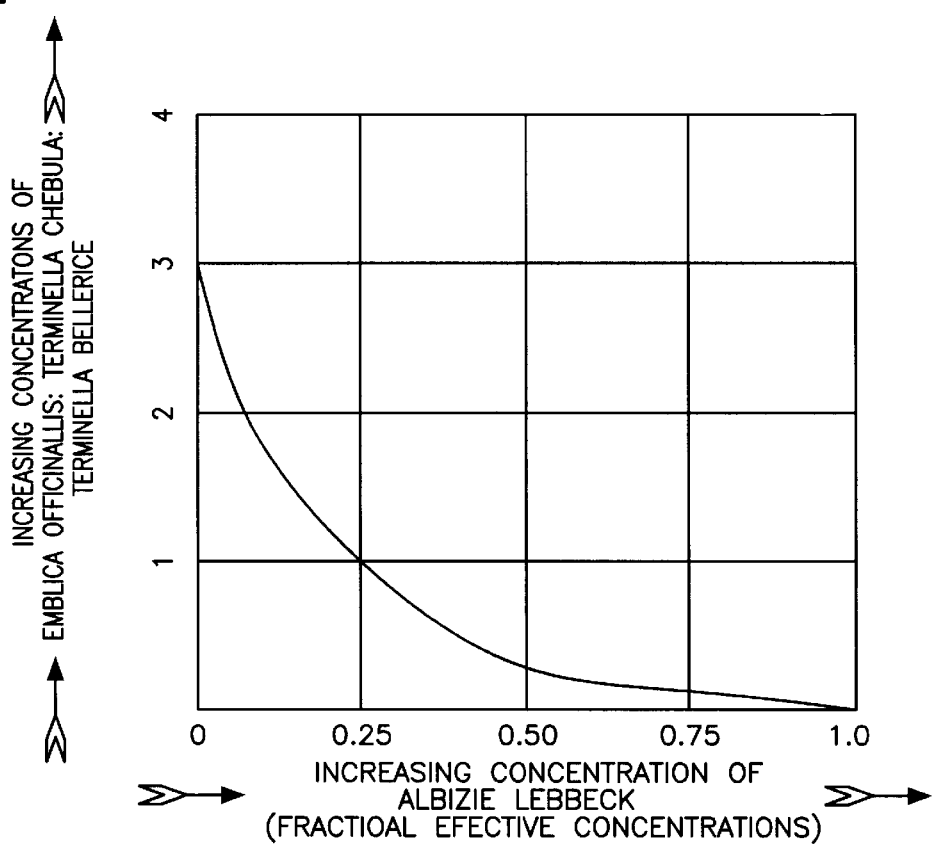

Based on these studies increasing concentrations of the extracts of *Emblica officinals* fruits, extracts of *Terminalia chebula* fruits, extracts of *Terminalia bellerica* fruits were plotted and tested against increasing concentrations of the extract of *Albizia lebbeck* bark and each of these combinations were tested in the mast cell stabilization assay. All these permutations and combinations, showed synergism and promising anti allergic activity. Amongst these combinations one of the combination in the ratio of 3:3:3:1 (*Emblica officinalis: Terminalia chebula: Terminalia bellerica: Albizia lebbeck*) was selected for further development of the invention, which is shown in FIG. 2.

From the table 1 above the remaining ingredients which showed potent mast cell stabilisation activity were selected (viz *Piper longum, Piper nigrum* and *Zingiber officinale*) for compatibility studies. It was found that the presence of extracts of the plants *Piper longum, Piper nigrum* and *Zingiber officinale* in the composition further enhanced the synergistic activity and the mast cell stabilisation activity of the resultant composition making it useful as antiallergic agent specifically for the treatment of allergic rhinitis and allergic asthma.

Accordingly, the present invention provides an improved synergistic herbal composition having anti allergic activity particularly for the treatment of allergic rhinitis and allergic asthma, which comprises the extracts of:

fruits of *Terminalia chebula* in an amount in the range of 15–50% w/w fruits of *Terminalia bellerica* in an amount in the range of 15–50% w/w bark of *Albizia lebbeck* in an amount in the range of 0.5–50% w/w fruits of *Emblica officinalis* in an amount in the range of 15–50% w/w According to another feature of the present invention the above composition also contains the extracts of:

fruits of *Piper longum* in an amount in the range of 0.1–5% w/w fruits of *Piper nigrum* in an amount in the range of 0.1–5% w/w rhizome of *Zingiber officinale* in an amount in the range of 0.1–5% w/w In an embodiment of the present invention the extracts of the plants employed may be water extracts.

In another embodiment of the present invention the extracts of the plants *Terminalia chebula, Terminalia bellerica, Albizia lebbeck* and *Emblica officinalis* employed may be water extracts and the extracts of the plants *Piper longum, Piper nigrum*, and *Zingiber officinale* employed may be alcoholic extracts.

The above composition of the present invention may also contain pharmaceutical excipients which are usually employed to prepare any oral dosage form like powder, tablets, capsules, syrups and liquids etc.

The excipients such as starch, pre-gelatinized starch, dicalcium phosphate or a mixture thereof may be used. The amount of excipients ranges from 30 to 60% w/w. The composition may also contain preservatives which may be selected from propyl paraben sodium, methyl paraben sodium or bronopol or a mixture thereof. The amount of preservatives employed may ranges from 0.1 to 1% w/w.

According to the present invention there is provided a process for the preparation of an improved synergistic herbal composition having anti allergic activity particularly for the treatment of allergic rhinitis and allergic asthma, which comprises mixing the extracts of fruits of *Terminalia chebula* in an amount in the range of 15–50% w/w fruits of *Terminalia bellerica* in an amount in the range of 15–50% w/w bark of *Albizia lebbeck* in an amount in the range of 0.5–50% w/w fruits of *Emblica officinalis* in an amount in the range of 15–50% w/w and drying the resultant mixture by conventional methods According to another feature of the invention the extracts of fruits of *Piper longum* in an amount in the range of 0.1–5% w/w fruits of *Piper nigrum* in an amount in the range of 0.1–5% w/w rhizomes of *Zingiber officinale* in an amount in the range of 0.1–5% w/w
are also added to the above said mixture and mixed thoroughly and the drying the resulting mixture.

In a preferred embodiment of the present invention, the drying may be effected by spray drying or by heating at a temperature in the range of 50–70° C. under vacuum.

In an embodiment of the invention the extracts of the plants employed for preparing the composition may be water extracts.

In another embodiment of the present invention the extracts of the plants *Terminalia chebula, Terminalia bellerica, Albizia lebbeck* and *Emblica officinalis* employed for preparing the composition are water extracts and the extracts of the plants *Piper longum, Piper nigrum* and *Zingiber officinale* employed are alcoholic extracts.

The above extracts can be prepared as per the conventional extraction procedures.

The excipients usually used in pharmaceutical preparations, may be added to the mixture to prepare modern dosage forms like tablets, capsules, powder, liquid, syrups etc. The excipients such as starch, pre-gelatinized starch, dicalcium phosphate or a mixture thereof may be used and the amount of excipients used may range from 30 to 60% w/w.

Preservatives may also be added to the mixture which when used may be selected from propyl paraben sodium, methyl paraben sodium or bronopol or a mixture thereof. The amount of the preservatives used may range from 0.1 to 1% w/w.

It would be very clear from the above said description that the composition of the present invention is not a mere admixture of the ingredients used resulting in a composition having the aggregate properties of the ingredients employed. The composition is a synergistic mixture of the ingredients having unique and profound antiallergic activity.

The invention is described in detail in the Examples given below which are provided by way of illustration only and therefore should not be construed to limit the scope of the invention.

EXAMPLE 1

An amount of 100 gms (30% w/w) of *Terminalia chebula*, 100 gms (30% w/w) of *Terminalia bellerica*, 30 gms (10% w/w) of *Albizia lebbeck* and 100 gms (30% w/w) of *Emblica officinalis*, were blended thoroughly. The resulting mixture was spray dried. To this mixture, 220 gms of a mixture of maize starch, pregelatinised starch and dicalcium phosphate (taken in equal quantities) is added as excipients and mixed thoroughly. The composition obtained is filled in hard gelatin capsules. Each capsule contains 330 mg of the active ingredients and can be used as a single or multiple doses as per the requirement for the treatment of allergic conditions. This composition for convenience is henceforth referred to as NR-A4

EXAMPLE-2

An amount of 115.5 gms (33% w/w) of *Terminalia chebula*, 115.5 gms (33% w/w) of *Terminalia bellerica*, 1.75 gms (0.5% w/w) of *Albizia lebbeck*, 115.5 gms (33% w/w) of *Emblica officinalis*, 0.58 gms (0.16% w/w) of *Piper longum*, 0.58 gms (0.16% w/w of *Piper nigrum* and 0.58 gms (0.16% w/w) of *Zingiber officinale* were blended thoroughly. The resulting mixture was dried at a temperature in the range of 55 to 60° C. under vacuum. This composition was made into powder having mesh size of 25 mesh. This composition in a dose of 350 mg can be used as a single or multiple doses for the treatment of allergic conditions as per the requirement This composition for convenience is henceforth referred to as NR-A1

EXAMPLE-3

An amount of 100 gms (30% w/w) of *Terminalia chebula*, 100 gms (30% w/w) of *Terminalia bellerica*, 25 gms (8% w/w) of *Albizia lebbeck*, 100 gms (30% w/w) of *Emblica officinalis*, 1.66 gms (0.66% w/w) of *Piper longum*, 1.66 gms (0.66% w/w) of *Piper nigrum* and 1.66 gms (0.66% w/w) of *Zingiber officinale*were blended thoroughly. The resulting mixture was dried at a temperature in the range of 55 to 60° C. under vacuum. To this mixture, 220 gms of a mixture of maize starch, pregelatinised starch and dicalcium phosphate (taken in equal quantities) is added as excipients and mixed thoroughly. The composition obtained is filled in hard gelatin capsules. Each capsule contains 330 mg of the active ingredients and can be used as a single or multiple doses as per the requirement for the treatment of allergic conditions. This composition for convenience is henceforth referred to as NR-A2

EXAMPLE-4

An amount of 56.25 gms (15% w/w) of *Terminalia chebula*, 56.25 gms (15% w/w) of *Terminalia bellerica*, 187.5 gms (50% w/w) of *Albizia lebbeck*, 56.25 gms (15% w/w) of *Emblica officinalis*, 6.25 gms (1.67% w/w) of *Piper longum*, 6.25 gms (1.67% w/w) of *Piper nigrum* and 6.25 gms (1.67% w/w) of *Zingiber officinale* were blended thoroughly. The resulting mixture was dried at a temperature in the range of 55 to 60° C. under vacuum. To this mixture, 225 gms of a mixture of maize starch, pregelatinised starch and dicalcium phosphate (taken in equal quantities) as excipients and 0.1 gm of methyl paraben sodium as preservative are added and mixed thoroughly The composition obtained is compacted into tablets by conventional method. Each tablet contains 375 mg of the active ingredients. The tablet can be used as a single or multiple doses as per the requirement for the treatment of allergic conditions. This composition for convenience is henceforth referred to as NR-A3

Each of the above said four compositions (NR-A1 to NR-A4) were again tested and compared using the mast cell stabilizing assay and the results are shown in the Table 2.

TABLE 2

The mast cell stabilizing activity of these selected prototypes was found to be as below.

| Test prototype | $EC_{50}$ (mcg/ml) |
| --- | --- |
| NR-A1 | 10.78 |
| NR-A2 | 6.49 |
| NR-A3 | 9.67 |
| NR-A4 | 15.64 |
| Disodiumchromoglycate (standard) | 3.66 |

In order to further confirm the synergistic activity of the composition of the present invention, all the four compositions explained in the Examples 1 to 4 were compared using four different in-vitro bioassays namely:
  i) Antihistaminic activity
  ii) Anti 5-Hydroxy tryptamine activity (Anti serotonin activity)
  iii) Trypsin inhibition assay
  iv) Free radical scavenging activity i) Anti histaminic activity: All the four compositions prepared by the process described in Examples 1 to 4 (NR-A1 to NR-A4) were evaluated on isolated guinea pig ileum. Guinea pig weighing 400 gms fasted for 48 hours with water ad libitum. On the day of experiment, it was sacrificed and ileum isolated. The terminal 10 cms of ileum was discarded. A small segment of ileum (2.5 cm) was isolated and mounted in water bath containing Tyrode's solution. The tissue was connected to a pressure transducer & the tracings were recorded using a multi channel polygraph. In the first step, a dose response curve was obtained with histamine starting from 0.05 mcg/35 ml up to the maximum dose of 2.5 mcg/35 ml. This ensured that the tissue was responding well. Solubilized antiallergic compositions were added at different doses viz., 100 mcg, 1 mg, 2 mg, 5 mg and 10 mg to see the blocking effect of histamine. All the four compositions have shown histamine-antagonizing property in isolated Guinea pig, ileum. In this context reference may be made to 1) Kulkarni, Hand book of Experimental Pharmacology $2^{nd}$ Edition (1993) Vallabh Prakshan Delhi 2) Ghosh M. N. "Fundamentals of Experimental pharmacology" $2^{nd}$ Edition—Chapter 26, 153–158 3) Akah P. A., et al, Journal of Ethnopharmacology, 55, 1997, 87–92).

TABLE 3

The antihistaminic activity of these compositions are shown below.

| Test prototype | $IC_{50}$ (mcg/ml) |
|---|---|
| NR-A1 | 106 |
| NR-A2 | 86 |
| NR-A3 | 274 |
| NR-A4 | 285 |
| Standard | 05 | ii) Anti 5-Hydroxy-tryptamine activity: All the four compositions prepared by the process described in the Examples 1 to 4 (NR-A1 to NR-A4) were evaluated on rat fundus strip. Albino wistar rat weighing 200 gms was fasted for 48 hrs with water ad-libitum. On the day of experiment it was sacrificed and fundus was isolated. The Upper fundus portion (pale coloured) was cut open and given alternate zigzag cuts to make a fundus strip of 2.5 cms and was mounted in the organ bath containing Tyrode physiological salt solution. The experiment conditions used were as follows.

| | |
|---|---|
| Temperature | 37–38° C. |
| Tension | 1 gm |
| pH | 7.4 |
| Aeration | Oxygen |

The tissue was connected to a force transducer and the contractions were recorded using a multi-channel polygraph. In the first step, a dose response curve was obtained with 5HT starting from 0.28 ng/ml up to the maximum dose of 7.14 ng/ml. This ensured that the tissue was responding well.

Solubilised antiallergic compositions were added at different doses of 100 mcg, 200 mcg, 400 mcg, 800 mcg, 1.6 mg, 3.2 mg, 6.4 mg and 12.8 mg to see the blocking effect of 5HT. It was found that the complete antagonism of 5HT was established by 12.8 mg of antiallergic composition/35 ml organ bath. The study was repeated 4 times and average of responses (% 5HT inhibition) was calculated to establish $IC_{50}$. The $IC_{50}$ was found to be 32.8 mcg/ml. In this context reference may be made to 1) Kulkarni, "Hand book of pharmacology" 2nd Edition (1993) Vallaba prakshan, Delhi 2) Ghosh M. N., fundamentals of experimental pharmacology, (1984) $2^{nd}$ Edition.

TABLE 4

Anti 5-Hydroxy-tryptamine activity

| Tested prototype | $IC_{50}$ (mcg/ml) |
|---|---|
| NR-A1 | 133 |
| NR-A2 | 75 |
| NR-A3 | 164 |
| NR-A4 | 175 |
| Standard | 10 | iii) Trypsin inhibition assay: Trypsin (Tryptase) is one of the preformed mediators liberated from mast cells on degranulation following antigen antibody reaction. Measurement of Trypsin activity indirectly measures mast cell stabilization. Reference may be made to Lavens S E, Proud, Warner J A (1993) J. Immunol. Met. 166(1): 93–102. This bioassay was performed as per the method of Canell R J P et al. (1988) Planta Medica, 54: 10–14, where porcine pancreas was used as the source of Trypsin and Benzoyl-D, L-4-nitroanilide was used as the substrate. The enzyme was incubated with the compositions NR-A1, NR-A2, NR-A3 & NR-A4 at different concentrations for 30 minutes of time and the substrate was added and again incubated for 60 minutes and the absorbance taken at 410 nm. The difference of absorbance when compared to the blank (without the drug) gave the extent of inhibition. Ovomucoide of egg white was used as the standard.

TABLE 5

Trypsin inhibition assay

| Test prototype | $EC_{50}$ (mcg/ml) |
|---|---|
| NR-A1 | 53.02 |
| NR-A2 | 44.46 |
| NR-A3 | 63.58 |
| NR-A4 | 75.65 |
| Standard | 32.36 | iv) Free radical scavenging: An antioxidant drug reacts with blue coloured 1,1-Diphenyl-2-picryl hydrazyl (DPPH) and reduces it to colourless 1,1-Diphenyl-2-picryl hydrazine. This is a colour reaction and can be read using a spectrophotometer at 570 nm. The reduction in absorbance gives the anti-oxidant activity. In this context reference may be made to 1) Kato K. et al, J. Med. Chem. 31, 1988, 793–798.

TABLE 6

The free radical scavenging activity of the four compositions NR-A1, NR-A2, NR-A3 & NR-A4 are given below.

| Test prototype | $EC_{50}$ (mcg/ml) |
|---|---|
| NR-A1 | 7.873 |
| NR-A2 | 5.623 |
| NR-A3 | 8.484 |
| NR-A4 | 9.832 |
| Standard | 3.475 |

PHARMACOLOGICAL ACTIVITIES OF NR-A2

The activity of NR-A2 was further confirmed in the following biological assays.

Efficacy Data

1] Anti-anaphylactic Activity

A] Effect on Active Anaphylaxis in Rats (Mesenteric Mast Cells):

The experiment was designed to induce active anaphylaxis in rats by sensitization with horse serum as the antigen and triple vaccine containing *B. pertusis* organisms (1 ml) as the adjuvant as per Tripathi et al.

The animals were divided into 4 groups. One served as sensitized control with no treatment [0.5% carboxy methyl cellulose (CMC)], the second served as sensitized group with standard Prednisolone at a dose of 10 mg/kg and the other two sensitized groups received NR-A2 in doses of 250 and 350 mg/kg body weight in 0.5% CMC, orally 30 days prior to sensitisation and 11 days after sensitisation.

Eleven days after sensitization, the rats were sacrificed, blood collected for passive anaphylaxis, mesenteries dissected out to observe mast cell degranulation. NR-A2 showed a dose dependent protection. Dose of NR-A2 at 250 mg/kg produced 49.38% ($P<0.05$) and 350 mg produced 56.35% protection ($p<0.05$).

The results demonstrated that, NR-A2 brings about anti-anaphylactic activity and this could be probably by inhibition of secretion of antibodies or mast cell stabilization or both. In this context the reference may be made to Tripathi R. M., Sen P. C. and Das P. K., (1979) *Journal of Ethnopharmacology* 385–396.

B] Passive Paw Anaphylaxis in Rats:

Similar to the above experiment, passive paw anaphylaxis was evaluated as per method of Gokhale A B & Saraf M N (2000), *Indian Drugs*, 37(5), 228–232. 0.15 ml of the anti-serum was administered to the right hind paw of female rats and the left paw was given an equal volume of saline. 24 hrs. after sensitisation, the rats were challenged with 0.15 ml of horse serum in the right hind paw. Paw volumes were measured using a Plethysmograph. Difference in the paw volume before and after antigen challenge gave the extent of anaphylaxis. NR-A2 at 250 mg/kg produced significant inhibition of 45.09, 33.48, 28.26% at 10, 30 and 60 minutes ($P<0.05$) respectively.

These results demonstrate that NR-A2 is an effective anti-inflammatory and mast cell stabilizer.

C] Active Paw Anaphylaxis in Mice:

Active paw anaphylaxis in mice was studied using egg albumin as the antigen adsorbed on aluminum hydroxide. In this context the reference may be made to Ghoosi R. B, Bhide M. B, (1981) *Allergy Appl. Immunol.*, 15, 53. and Nair A. M. et al. (1995) *Indian Drugs*, 32(6), 277–282. The mice were dosed with NR-A2 at different doses orally in 0.5% CMC for 30 days. Prednisolone was taken as the standard. On $31^{st}$ day they were sensitized with antigen, and the treatment continued. On $12^{Th}$ day after sensitization the animals were re-challenged with egg albumin in saline subcutaneously in plantar region of right hind paw while the contralateral paw received an equal volume of saline. Paw thickness was measured using pocket thickness gauge (Mitutoyo Manufacturing Co. Japan) 15 minutes after the challenge. The difference in paw thickness of right paw compared to the left paw, reflected the edema due to antigen-antibody reaction.

NR-A2 produced a dose dependent inhibition of paw edema ($P<0.05$ for all doses) with an $ED_{50}$ of 134.9 mg/kg mouse body weight. Prednisolone produced an inhibition of 74.03% at a dose of 14 mg/kg body weight ($P<0.05$). These results demonstrate that NR-A2 is an effective anti-inflammatory and mast cell stabilizer.

D] Dale-Schultz Phenomenon in Guinea Pig Tracheal Chain (In-Vitro):

NR-A2 was tested for anti-anaphylatic activity in Guinea pigs using tracheal strips in-vitro. In this context the reference may be made to Adolf Meister et al, 1999, "Antispasmodic activity of *Thymus vulgaris* extract on the isolated Guinea pig trachea: Discrimination between drug and ethanol effects", *Plata Medica*, 65, 512–516. NR-A2 showed dose dependant inhibition with an $IC_{50}$ of 16.496 mcg/ml. Investigations on NR-A2 revealed marked dose-dependent anti-spasmodic activity against spasm induced by antigen.

E] Dale-Schultz Phenomenon in Guinea Pig Ileum:

Dale Schultz phenomenon refers to generation of a secondary immune response in sensitized Guinea pigs. In response to horse serum (antigen), IgG antibodies are produced which combine with mast cells on the mucosal and submucosal tissues of Guinea pig ileum. On rechallenge, there is mast cell degranulation. The mediators released cause contraction of Guinea pig ileum. The important mediators involved in spasmodic contraction of the ileum are histamine and leucotrienes. In this model Guinea pig ileum was taken to study anaphylaxis. 12 Guinea pigs were divided into two groups, control and treated. Control group received vehicle CMC and treated group received NR-A2 in the dose of 511.4 mg/kg for 30 days prior to sensitization. Sensitization was done with intra peritoneal injection of horse serum. 21 days after sensitization, animals were sacrificed and ileum strips were mounted in isolated organ bath by the method of Magus.

Responses to rechallenge with the antigen (Horse Serum) were recorded for 90 seconds, after confirming tissue sensitivity with histamine before and after the challenge. Tissues from all sensitized groups showed spasmodic effect, while out of five animals in NRA2 group it was negative in two, in two animals it was sluggish and in the remaining one animal it was positive. These results demonstrate that NR-A2 can probably reduce the synthesis of specific antibodies to a certain extent which shows that NR-A2 is a promising anti-allergic product. For further details reference may be made to Tripathi R. M., Sen P. C. and Das P. K., *Journal of Ethnopharmacology* (1979) 385–396 and Magnus cited by Ghosh, M. N. (1984), 'Fundamentals of Experimental Pharmacology' $2^{nd}$ Edition, 34.

F] Systemic Anaphylaxis in Rats:

The effect of NR-A2 in compound 48/80 (Condensation product of N-methyl-p-methoxyphenylamine with formaldehyde) induced systemic anaphylaxis was studied in rats. In this context the reference may be made to Y. M. Lee, Kim D. K, (1996) *Journal of Ethnopharmacology*, 54, 77–84. The animals were divided into five groups, one served as control, one standard and three groups for NR-A2. The standard (Prednisolone), NRA-2 & vehicle were given 30 days prior to intra-peritoneal administration of compound 48/80 (Condensation product of N-methyl-p-methoxyphenylamine with formaldehyde). The dose of Prednisolone was 10 mg/kg while those of NR-A2 were 150, 250, 350 mg/kg b.w. Number of deaths per group within one hour were calculated. NR-A2 inhibited compound 48/80 (Condensation product of N-methyl-p-methoxyphenylamine with formaldehyde) induced anaphylaxis in a dose dependent manner with an inhibition of 44.45% at a dose of 350 mg/kg rat body weight. Standard Prednisolone showed 62.97% inhibition. These results demonstrate that NR-A2 is an effective mast cell stabilizer.

G] Compound 48/80 (Condensation Product of N-methyl-p-methoxyphenylamine With Formaldehyde) Induced Mouse Paw Edema:

Compound 48/80 (Condensation product of N-methyl-p-methoxyphenylamine with formaldehyde) was used to induce mouse paw edema in mice. In this context the reference may be made to Nair A M, Tamhankar C P and Saraf M N (1995) *Indian drugs*, 32(6), 277–282. The animals were treated with NR-A2 at doses of 175, 225 and 275 mg/kg body weight orally 30 days prior to the test. Standard group received Ketotifen in the dose of 1 mg/kg b.w. NR-A2 produced dose dependent inhibition (P<0.05 for all the doses) of paw edema with an EDM of 562.3 mg/kg body weight. Ketotifen produced 64.22% inhibition (P<0.05) at the dose of 1 mg/kg mouse body weight.

These results demonstrate that NR-A2 is an effective anti-inflammatory product and mast cell stabilizer.

2] Anti Inflammatory Activity

A] Acute-Inflammation Carragennan Induced Rat Paw Edema:

Carragennan, an irritant is a polysaccharide isolated from chondrus. When injected into the hind paw of rat, it causes edema which reaches peak at 4 hrs and subsides within 24 hrs completely. In this context the reference may be made to Winter C A, Risley E A, and Nuss G W (1962) *Proc. Soc. Exp. Biol. med.*, 111, 544. The difference in the volume of foot at 4 hrs after injection and before indicates the amount of inflammation. Mediators involved in the response are prostaglandins, histamine and active oxygen species.

NR-A2 produced significant anti-inflammatory effect at an oral dose of 120 mg/kg-mouse body weight. There was 31.3% inhibition compared to the control (P<0.05)

B] Adjuvant Induced Arthritis

Freund's adjuvant is a mixture of dead mycobacterium finely ground in liquid paraffin at a concentration of 5 mg/ml. When injected in hind paw it produces an edema characterised as a bi-phasic response, which persists up to 21 days. The injection of Freund's adjuvant in rat hind paw produces conditions similar to rheumatoid arthritis, a delayed hypersensitivity reaction. In this context the reference may be made to Pearson C M, Wood F D (1959), *Arthr Rheum*, 2; 440–459 Hence this model was chosen to evaluate the effect of NR-A2 on delayed hypersensitivity.

NR-A2 was administered to albino wistar rats orally at doses of 150, 250 and 350 mg to body weight for 30 days before and 21 days after injecting Freund's adjuvant. Paw volume was measured using plethesmograph. An $ED_{50}$ of 257.03 mg/kg body weight was observed. Prednisolone was used as a standard which produced an inhibition of 95.63% (P<0.05).

These results demonstrate that NR-A2 is a promising anti-allergic agent.

Toxicity Data

General Pharmacology of the composition NR-A2 was evaluated in rat ECG, rat blood pressure, isolated frog's heart, isolated frog rectus abdominis muscle and dog blood pressure models. No toxic effects were observed at recommended dose (Homiburger F. "In vivo testing in the study of toxicology and safety evaluation: A guide to General toxicology", Chapter 16, 268–293).

Other toxicity studies that were done were $LD_{50}$ determination. (Ghosh M. N (1984), In: Fundamentals of experimental pharmacology-toxicity studies—Chapter 26, $2^{nd}$ edition, 153–158.) and repeat dose toxicity studies (Organisation for Economic Co-operation and Development (OECD), 407, adopted on $27^{th}$ Jul., 1995). $LD_{50}$ was found to be above 1500 mg/kg in mice and repeat dose toxicity revealed no toxic symptoms up to a dose of 270 mg/kg body weight administered over a period of 21 days.

Preliminary Open Clinical Trial on Effect of the Composition Referred to as NRA2 (Described in Example 3)

(Anti-Allergic Composition) in Human Subjects

1) OBJECTIVE: To evaluate efficacy and safety of Example 3 in patients with allergic rhinitis with or without allergic bronchitis 2) STUDY PLAN:
   No. of patients: 18 patients were selected for the study.
   Age group: 9–60 years.
   Inclusion/exclusion criteria:
      Random selection
      Both sexes are included.
      Patients with chronic systemic diseases like diabetes, hypertension, Tuberculosis were excluded from study.
   Dose: 2 to 6 capsules/day.
   Duration: 3 to 6 months.
   Parameters used for assessment:
      Subjective Scoring in all 18 patients.
      Objective evaluation [IgE (Immuno globulin E) and AEC (Absolute Eosinophilic Count)] in 9 patients.
      Safety evaluation in 9 patients (Bio chemical investigations).

Following Evaluation Form was Used

| Name of the patient: | Age: | Sex: |
|---|---|---|
| Address: | Occupation: | |
| Date of commencement: | Date of completion: | |
| Chief complaints with duration: | | |

| Sl. No | Parameter | 0 Day | $90^{th}$ Day | $180^{th}$ Day |
|---|---|---|---|---|
| 01. | Sneezing | | | |
| 02. | Running Nose. | | | |
| 03. | Stuffy Nose | | | |
| 04. | Watering of eyes | | | |
| 05. | Wheeze. | | | |
| 06. | Cough. | | | |
| 07. | Breathlessness. | | | |
| 08. | Use of Bronchodilator puffs | | | |
| 09. | Use of Steroid Puffs | | | |
| 10. | Oral Medications | | | |
| | Total. . . | | | |

| Score for 1–7: | Score for 8–9: | | | |
|---|---|---|---|---|
| 0 - Nil | 8) Use of bronchodilatory puffs - Score | | 9) Use of Steroid Puffs | |
| 1 - Miid | | | | |
| 2 - Moderate | 0 | No usage - Nil | 0 | No usage - Nil |
| 3 - Severe | 1 | Occasional - once in 2–3 days or less - Mild | 1 | Occasional - once in 2–3 days or less - Mild |
| | 2 | Regular use 1–2 puffs per day - Moderate | 2 | Regular use 1–2 puffs per day - Moderate |
| Score for 10: | 3 | More than 2 puffs per day - Severe | 3 | More than 2 puffs per day - Severe |
| 0 - Not required | | | | |
| 1 - Occasional use (once in 1–2 days) | | | | |
| 2 - Regular use in therapeutic dose | | | | |

3) RESULTS:

3.1) Evaluation of symptomatic relief in patients with Allergic Rhinitis:

a) 9 patients out of 18 (50%) showed above 70% improvement.

b) 6 patients out of 18 (33%) showed 50–70% improvement.

c) 3 patients out of 18 (17.1%) showed below 50% improvement.

Results are shown in Table No. 1.

TABLE No.1

EVALUATION OF SYMPTOMATIC RELIEF IN PATIENTS WITH ALLERGIC RHINITS

| Patient Reg. No. | Duration of the treatment | Total Score Before | Total Score After | Percentage relief |
|---|---|---|---|---|
| 1. | 6 months | 11 | 5 | 54.55% |
| 2. | 6 months | 11 | 3 | 81.81% |
| 3. | 6 months | 19 | 1 | 94.7% |
| 4. | 6 months | 8 | 0 | 100% |
| 5. | 6 months | 14 | 3 | 78.5% |
| 6. | 6 months | 14 | 1 | 92.8% |
| 7. | 6 months | 20 | 8 | 60% |
| 8. | 6 months | 14 | 3 | 78.5% |
| 9. | 3 months | 7 | 0 | 100% |
| 10. | 3 months | 12 | 5 | 58.3% |
| 11. | 3 months | 6 | 4 | 33.33% |
| 12. | 3 months | 7 | 5 | 17.66% |
| 13. | 3 months | 9 | 1 | 88.8% |
| 14. | 3 months | 17 | 8 | 53% |
| 15. | 3 months | 11 | 4 | 63% |
| 16. | 3 months | 5 | 0 | 100% |
| 17. | 3 months | 13 | 1 | 92.3% |
| 18. | 3 months | 13 | 5 | 62% |

3.2) Objective Evaluation:

a) 8 out of 9 patients showed reduction IgE levels. There was an increase in 1 patient.

b) 4 out of 9 patients showed reduction in AEC (absolute Eosinophilic count) levels and 5 showed increase in levels.

Results are shown in Table No. 2.

TABLE No. 2

OBJECTIVE EVALUATION IN PATIENTS WITH ALLERGIC RHINITIS

| Patient Reg. No. | Duration of the treatment | IgE Before | IgE After | AEC Before | AEC After |
|---|---|---|---|---|---|
| 1. | 6 months | 1127 | 622 | 1530 | 630 |
| 2. | 6 months | 519 | 447 | 1150 | 480 |
| 3. | 6 months | 750 | 725 | 1120 | 1026 |
| 4. | 6 months | 262 | 254 | 380 | 434.5 |
| 5. | 6 months | 369 | 400 | 600 | 484 |
| 6. | 6 months | 493.7 | 321.0 | 600 | 680 |
| 7. | 6 months | 642 | 479 | 570 | 850 |
| 8. | 3 months | 72 | 63 | 200 | 585 |
| 9. | 3 months | 104 | 103 | 260 | 452 |

IgE - Immuno globulin E
AEC - Absolute eosinophil count

1) CONCLUSION:

The composition designated as NR-A2 is a safe and efficacious poly herbal formulation. Similarly the other three compositions namely NRA1, NRA3 & NRA4 were evaluated and found that they are also safe and effective antiallergic agents particularly in the treatment of allergic rhinitis and allergic asthma. Likewise the composition envisaged within the scope of the present invention have been found to be very useful as anti allergic agents especially for the treatment of allergic rhinitis and allergic asthma.

Dose:

As explained earlier the composition can be in the form of capsules, tablets, powder syrups & liquids for the purpose of administration. The dose of the composition may vary according to the requirements of the patients. The dosage may, preferably be, from 330 mg to 3000 mg per day in divided doses according to the severity of the disease.

Advantages of the Present Invention

The composition is very effective as antiallergic agent particularly in allergic rhinitis and allergic asthma The composition is effective even in small dose and can also be administered in any dosage form The composition is palatable The composition is very safe and has reduced side effects

What is claimed is:

1. A synergistic antiallergic herbal composition which comprises the extracts of fruits of *Terminalia chebula* in an amount in the range of 15–50% w/w fruits of *Terminalia bellerica* in an amount in the range of 15–50% w/w bark of *Albizia lebbeck* in an amount in the range of 0.5–50% w/w fruits of *Emblica officinalis* in an amount in the range of 15–50% w/w.

2. The composition as claimed in claim 1 wherein the composition also contains the extracts of fruits of *Piper longum* in an amount in the range of 0.1–5% w/w fruits of *Piper nigrum* in an amount in the range of 0.1–5% w/w rhizomes of *Zingiber officinale* in an amount in the range of 0.1–5% w/w.

3. The composition as claimed in claim 1 wherein the extracts of the plants employed are water extracts.

4. The composition as claimed in claim 2 wherein the extracts of the plants *Terminalia chebula*, *Terminalia bellerica*, *Albizia lebbeck* and *Emblica officinalis* employed are water extracts and the extracts of the plant *Piper longum*, *Piper nigrum* and *Zingiber officinale* employed are alcoholic extracts.

5. The composition as claimed in claim 1, further comprising a pharmaceutically acceptable excipient for an oral dosage form.

6. The composition as claimed in claim 5, wherein the excipient is selected from starch, pre-gelatinized starch, dicalcium phosphate or a mixture thereof.

7. The synergistic composition as claimed in claim 5 wherein the amount of excipient employed ranges from 30 to 60% w/w.

8. The composition as claimed in claim 1 wherein the composition also contains a preservative selected from propyl paraben sodium, methyl paraben sodium or bronopol or a mixture thereof.

9. The composition as claimed in claim 8 wherein the amount of preservative used ranges from 0.1 to 1% w/w.

10. A process for preparing a synergistic antiallergic herbal composition which comprises mixing thoroughly the extracts of fruits of *Terminalia chebula* taken in the range of 15–50% w/w fruits of *Terminalia bellerica* taken in the range of 15–50% w/w bark of *Albizia lebbeck* taken in the range of 0.5–50% w/w fruits of *Emblica officinalis* taken in the range of 15–50% w/w and drying the resultant mixture.

11. A process for the preparation of a synergistic composition as claimed in claim 10 wherein extracts of Fruits of *Piper longum* taken in the range of 0.1–5% w/w
Fruits of *Piper nigrum* taken in the range of 0.1–5% w/w
Rhizomes of *Zingiber officinale* taken in the range of 0.1–5% w/w are also added and the resultant mixture is mixed thoroughly.

12. A process for the preparation of a synergistic composition as claimed in claim 10 wherein the drying is effected by spray drying or by heating at a temperature in the range of 50–70° C. under vacuum.

13. A process as claimed in claim 10 wherein a pharmaceutically acceptable excipient is added to the mixture.

14. A process as claimed in claim 13 wherein the excipient is selected from starch, pre-gelatinized starch, dicalcium phosphate or a mixture thereof.

15. A process as claimed in claim 10 wherein the amount of excipients ranges from 30 to 60% w/w.

16. A process as claimed in claim 10 wherein preservative is added to the mixture, the preservative being selected from propyl paraben sodium, methyl paraben sodium or bronopol or a mixture thereof.

17. A process as claimed in claim 16 wherein the amount of preservative used ranges from 0.1 to 1% w/w.

18. A method of treating a subject suffering from an allergic condition which comprises administering to the subject the composition as claimed in claim 1.

19. The method according to claim 18, wherein the subject is suffering from a condition selected from rhinitis and asthma.

* * * * *